United States Patent
Garudadri et al.

(10) Patent No.: US 11,123,013 B2
(45) Date of Patent: Sep. 21, 2021

(54) HYPERTONICITY MEASURING DEVICE AND METHOD

(71) Applicant: The Regents of the University of California, Oakland, CA (US)

(72) Inventors: Harinath Garudadri, La Jolla, CA (US); Andrew Skalsky, La Jolla, CA (US); Tse Nga Ng, La Jolla, CA (US); Michael Yip, La Jolla, CA (US); Leanne Chukoskie, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 681 days.

(21) Appl. No.: 15/807,380

(22) Filed: Nov. 8, 2017

(65) Prior Publication Data

US 2018/0125425 A1    May 10, 2018

Related U.S. Application Data

(60) Provisional application No. 62/419,056, filed on Nov. 8, 2016.

(51) Int. Cl.
*A61B 5/11*        (2006.01)
*A61B 5/00*        (2006.01)
(Continued)

(52) U.S. Cl.
CPC .............. *A61B 5/6828* (2013.01); *A61B 5/30* (2021.01); *A61B 5/6825* (2013.01);
(Continued)

(58) Field of Classification Search
CPC .... A61B 5/6802; A61B 5/6804; A61B 5/6806
See application file for complete search history.

(56) References Cited

U.S. PATENT DOCUMENTS

2005/0005703 A1* 1/2005 Saito .................. G01L 9/12
                                                73/780
2013/0197399 A1   8/2013 Montgomery
(Continued)

FOREIGN PATENT DOCUMENTS

WO      91/07214 A1    5/1991
WO    2011/110997 A2   9/2011
WO    2016/109744 A1   7/2016

OTHER PUBLICATIONS

Skalsky AJ, Vadivelu S, Dalal P., "Spasticity Management", Physical Medicine and Rehabilitation. Chapter 274 (In press; pre-publication on manuscript submitted),(17 pages total).
(Continued)

*Primary Examiner* — Puya Agahi
(74) *Attorney, Agent, or Firm* — Stuart H. Mayer; Mayer & Williams PC (57) ABSTRACT

A hypertonicity measuring device comprises at least one wearable item. The hypertonicity measuring device comprises at least one communication pathway. The at least one communication pathway is configured to communicate with a processing device. The hypertonicity measuring device comprises a sensor array. The sensor array is disposed to the at least one wearable item. The sensor array comprises a plurality of capacitive pressure sensors. The sensor array is configured to communicate capacitive pressure sensor data to the processing device employing the at least one communication pathway. The plurality of capacitive pressure sensors comprises at least one structured dielectric. The hypertonicity measuring device comprises an inertial measurement unit. The inertial measurement unit is disposed to the at least one wearable item. The inertial measurement unit is configured to communicate motion data to the processing device employing the at least one communication pathway.

8 Claims, 6 Drawing Sheets

(51) Int. Cl.
    *A61B 5/30*      (2021.01)
    *A61B 5/107*     (2006.01)
(52) U.S. Cl.
    CPC ........... *A61B 5/1071* (2013.01); *A61B 5/1107* (2013.01); *A61B 5/1121* (2013.01); *A61B 5/1124* (2013.01)

(56) References Cited

U.S. PATENT DOCUMENTS

| | | |
|---|---|---|
| 2015/0091859 A1 | 4/2015 | Rosenberg et al. |
| 2016/0054798 A1 | 2/2016 | Messingher et al. |
| 2016/0175683 A1* | 6/2016 | Caroll-James ....... A63B 71/145 700/91 |
| 2017/0086686 A1* | 3/2017 | Narasimhan ......... A61B 5/6831 |
| 2017/0189752 A1* | 7/2017 | Mohrman ............ A61B 5/7271 |
| 2018/0140244 A1* | 5/2018 | Lin ..................... A61B 5/0053 |
| 2018/0154140 A1* | 6/2018 | Bouton ................ A61B 5/0488 |

OTHER PUBLICATIONS

Skalsky AJ, Fournier CM., "Intrathecal Baclofen Bolus Dosing and Catheter Tip Placement in Pediatric Tone Management", Phys Med Rehabil Clin N Am. Feb. 2015; 26(1):89-93. doi: 10.1016/j.pmr. 2014.09.011. Review. PubMed PMID: 25479782. (5 pages total).
Deon LL, Gaebler-Spira D., "Assessment and treatment of movement disorders in children with cerebral palsy", Orthop Clin North Am. Oct. 2010; 41(4):507-17. (11 pages total).
Ashworth B., "Preliminary trial of carisoprodol in multiple sclerosis", Practitioner 1964; 192:540-2. (3 pages total).
Bohannon RW, Smith MB., "Interrater reliability of a modified Ashworth scale of muscle spasticity", Physical Therapy, Feb. 1987; 67:206-7. (2 pages total).
Pandyan AD, Johnson GR, Price CI, et al., "A review of the properties and limitations of the Ashworth and modified Ashworth Scales as measures of spasticity", Clinical Rehabilitation, 1999; 13:373-83. (11 pages total).
Fosang AL, Galea MP, McCoy AT, Reddihough DS, Story I., "Measures of muscle and joint performance in the lower limb of children with cerebral palsy". Developmental Medicine & Child Neurology, Oct. 2003; 45(10):664-70. (7 pages total).
JFM Fleuren et al., "Stop using the Ashworth Scale for the assessment of spasticity". J. Neurol Neurosurg Psychiatry 2010;81:46- 52,Sep. 21, 2009 (18 pages total).
Wu, Yi-Ning, Hyung Soon Park, Yupeng Ren, Deborah Gaebler-Spira, Jia-Jin Chen, and Li-Qun Zhang. "Measurement of elbow spasticity in stroke patients using a manual spasticity evaluator." In Engineering in Medicine and Biology Society, 2006. EMBS'06. 28th Annual International Conference of the IEEE, pp. 3974-3977. IEEE, 2006. (4 pages total).
Park, Hyung-Soon, Qiyu Peng, and Li-Qun Zhang, "A portable telerehabilitation system for remote evaluations of impaired elbows in neurological disorders." IEEE Transactions on Neural Systems and Rehabilitation Engineering 16, No. 3 (Jun. 2008): 245-254 (10 pages total).
Xin, Zhang, Norimasa Adachi, and Kazunori Hase. "A computed model for quantitative evaluation of spasticity in man." In Computational Engineering in Systems Applications, IMACS Multiconference on, vol. 2, pp. 1844-1847. IEEE, Oct. 2006. (4 pages total).
Grow, David I., Mengnan Wu, Michael J. Locastro, Sugandha K. Arora, Amy J. Bastian, and Allison M. Okamura. "Haptic simulation of elbow joint spasticity," In Mar. 2008 Symposium on Haptic Interfaces for Virtual Environment and Teleoperator Systems, pp. 475-476. IEEE, 2008. (2 pages total).
Park, Hyung-Soon, Jonghyun Kim, and Diane L. Damiano. "Development of a haptic elbow spasticity simulator (HESS) for improving accuracy and reliability of clinical assessment of spasticity." IEEE transactions on neural systems and rehabilitation engineering 20, No. 3 (2012): 361-370. (28 pages total).
Park, Hyung-Soon, Jonghyun Kim, and Diane L. Damiano. "Haptic recreation of elbow spasticity." In 2011 IEEE International Conference on Rehabilitation Robotics, pp. 1-6. IEEE, 2011 (17 pages total).
Kim, Jonghyun, Hyung-Soon Park, and Diane L. Damiano. "Accuracy and reliability of haptic spasticity assessment using HESS (haptic elbow spasticity simulator)." In 2011 Annual International Conference of the IEEE Engineering in Medicine and Biology Society, pp. 8527-8530. IEEE, 2011.(12 pages total).
Zakaria, Noor Ayuni Che, Takashi Komeda, Cheng Yee Low, Fazah Akhtar Hanapiah, and Kaoru Inoue. "Spasticity mathematical modelling in compliance with modified Ashworth scale and modified Tardieu scales." In Control, Automation and Systems (ICCAS), 2015 15th International Conference on, pp. 1893-1897. IEEE, 2015. (5 pages total).
Ishikawa, Shun, Shogo Okamoto, Kaoru Isogai, Yasuhiro Akiyama, Naomi Yanagihara, and Yoji Yamada. "Wearable dummy to simulate joint impairment: severity-based assessment of simulated spasticity of knee joint." In System Integration (SII), 2013 IEEE/SICE International Symposium on, pp. 300-305. IEEE, Dec. 2013. (6 pages total).
Ferreira, João, Vitor Moreira, José Machado, and Filomena Soares. "Improved biomedical device for spasticity quantification." In Bioengineering (ENBENG), 2013 IEEE 3rd Portuguese Meeting in, pp. 1-4. IEEE, Feb. 2011 (4 pages total).
Misgeld, Berno JE, Markus Lüken, Daniel Heitzmann, Sebastian I. Wolf, and Steffen Leonhardt. "Body-Sensor-Network-Based Spasticity Detection." IEEE journal of biomedical and health informatics 20, No. 3 (May 2016): 748-755. (8 pages total).
Peng, Qiyu, Parag Shah, Ruud W. Selles, Deborah J. Gaebler-Spira, and Li-Qun Zhang. "Measurement of ankle spasticity in children with cerebral palsy using a manual spasticity evaluator." In Engineering in Medicine and Biology Society, 2004. IEMBS'04. 26th Annual International Conference of the IEEE, vol. 2, pp. 4896- 4899. IEEE, 2004. (4 pages total).
Sherwood, Arthur M., M. M. Priebe, and W. B. McKay. "Quantification of surface electromyographic recordings for assessment of spasticity." In Engineering in Medicine and Biology Society, 1996. Bridging Disciplines for Biomedicine. Proceedings of the 18th Annual International Conference of the IEEE, vol. 2, pp. 597-598. IEEE. (2 pages total).
"Grip System", Tekscan, Retrieved from: https://www.tekscan.com/ print/products-solutions/systems/grip-system, Retrieved on: Jun. 5, 2018 (8 pages total).
MotionNode, "MotionNode Miniature Inertial Measurement Unit" 2017, Retrieved from: http://www.motionnode.com/, Retrieved on: Jun. 5, 2018 (2 pages total).
SparkFun Load Cell Amplifier—HX711, SEN-13879—SparkFun Electronics, Retrieved from: https://www.sparkfun.com/products/ 13879, Retrieved on: Jun. 5, 2018 (9 pages total).
Potentiometers Line Guide, Sensing and Control: Honeywell, Nov. 2014, Retrieved from: sensing.honeywell.com (12 pages total).
Orfanidis, Sophocles J., "Introduction to Signal Processing," Rutgers University, Englewood Cliffs, NJ: Pearson Education, Inc. Copyright ©1996-2009 by Prentice Hall, Inc. 1996. (795 pages total).
J. Lance, "Spasticity: Disordered Motor Control" R. Feldman, R. Young, and Koella, Eds. Year Book Medical Publishers, p. 961, 1980 (1 page total).
R. W. Bohannon and M. B. Smith, "Interrater reliability of a modified Ashworth Scale of muscle spasticity," Physical Therapy., vol. 67, No. 2, pp. 206-207, Feb. 1987. (2 pages total).
Wettenschwiler, Patrick D., Rolf Stämpfli, Silvio Lorenzetti, Stephen J. Ferguson, René M. Rossi, and Simon Annaheim. "How reliable are pressure measurements with Tekscan sensors on the body surface of human subjects wearing load carriage systems?", International Journal of Industrial Ergonomics 49 (2015): 60-67. (8 pages total).
Kim, J., Ng, T. N., Kim, W. S. "Highly Sensitive Tactile Sensors Integrated with Organic Transistors", Applied Physics Letters, 101, 103308, 2012. (6 pages total).

* cited by examiner

HYPERTONICITY MEASURING DEVICE AND METHOD

CROSS-REFERENCE TO RELATED APPLICATION

This application claims benefit and priority to U.S. Provisional Application No. 62/419,056, filed Nov. 8, 2016, entitled, "Hypertonicity Measuring Device", which is incorporated herein by reference in its entirety.

BACKGROUND

Spasticity is a debilitating condition and the most common physical symptom of acquired brain injury, stroke, or other neuro-muscular disorders such as cerebral palsy and affects more than 17 million people worldwide. Patients with spasticity are unable to produce smooth and fluid limb movements due to the imbalance of signals from the brain and spinal cord to the muscles. The pharmaceutical industry spends billions of dollars developing drugs to relieve spasticity, but these efforts are stymied by the lack of repeatable, objective metrics to quantify the outcomes; excessive dosage of drugs to treat spasticity can cause severe side effects such as such as seizures, blurred vision, and severe rashes, while inadequate dosage is ineffective at treating spasticity.

The current benchmark for assessing spasticity is the 6-point modified Ashworth score (MAS). There are several limitations to the MAS, including poor inter-rater reliability and poor sensitivity to changes in spasticity.

Many researchers have taken different approaches to address the lack of quantitative assessment of spasticity. Wearable devices and electromyography (EMG) sensors have been deployed on patients to detect spasticity symptoms, but the drawback is that such devices can be inconvenient and uncomfortable for the patient.

EMG sensors may be employed on patients to detect muscle tone. Studies using EMG sensors were carried out on patients with spasticity to characterize the patients' muscle tones under flexion and extension. Wu et al. However, many EMG sensors may not provide measurements with a high enough resolution to detect subtle changes in hypertonicity.

Force sensors may be employed to measure forces. Many existing force sensors may not provide measurements with a high enough resolution to detect subtle changes in hypertonicity. Many existing force sensors (e.g. resistive force sensors) may be affected by environmental temperatures.

Some researchers have measured the catch angle reliably by determining the instantaneous velocity and the time derivative of torque. Other research also targeted measurement of catch angle and elbow range of motion. Both of these studies were focused on identifying the presence/absence of a catch phase for correlation to a MAS score between 1 and 2, but these studies did not provide a continuous scale to quantify the different levels of severity.

The lack of a quantitative scale for spasticity was addressed by development of musculoskeletal models or haptic simulations to determine key physical parameters that contribute to spasticity. One of the most common models is the Haptic Elbow Spasticity Simulator (HESS), in which the properties of spasticity are simulated with the muscle resistance as torque and the catch phase as an impulse. Development of the HESS simulator mainly benefits the doctors as they can practice MAS assessments without requiring actual patients. Their research focused on modeling of spasticity and emphasized the factors that characterized each MAS level. Alternatively, a mathematical model by Zakaria et al. formulated the resistance as torque and accounted for additional parameters such as the angular velocity, modulus of elasticity etc. The above models have yet to be translated into physical tests that can be implemented on patients to track the spectrum of spasticity conditions.

In one aspect, the invention is directed to a hypertonicity measuring device, including: at least one wearable item; at least one communication pathway configured to communicate with a processing device; a sensor array, such that the sensor array is disposed to the at least one wearable item; including a plurality of capacitive pressure sensors, the plurality of capacitive pressure sensors including at least one structured dielectric; and configured to communicate capacitive pressure sensor data to the processing device employing the at least one communication pathway; and an inertial measurement unit: disposed to the at least one wearable item; and configured to communicate motion data to the processing device employing the at least one communication pathway.

Implementations of the invention may include one or more of the following. The at least one wearable item may include at least one of the following: an article of clothing; a synthetic material; and a leather material. The processing device may include at least one of the following: a frequency division multiplexing circuit; a multiplexor; an analog to digital converter; an output device; and a remote device. At least some of the plurality of capacitive pressure sensors may be configured for femtofarad resolution. At least one structured dielectric may include at least one of the following structures: a honeycomb structure; a hemispherical structure; nano-needle structure; and a structure including a plurality of pillars. The capacitive pressure sensor data may include force measurements. The inertia measurement unit may include at least one of the following: an accelerometer; a gyroscope; and a magnetometer. The motion data may include measurements of at least one of the following: at least one magnetic field; linear acceleration; angular acceleration; linear velocity; and angular velocity. The processing device may be configured to estimate a power based, at least in part, on: the capacitive pressure sensor data; and the motion data.

In another aspect, the invention is directed to a method of manufacturing a sensor array including a plurality of capacitive pressure sensors, the method including: depositing at least one conductive material onto a wearable item, the depositing of the at least one conductive material configured to cause formation of the following: a plurality of electrodes; and at least a portion of at least one communication pathway; and depositing at least one dielectric material onto the wearable item, the depositing of the at least one dielectric material configured to cause formation of at least one structured dielectric.

Implementations of the invention may include one or more of the following. The at least one conductive material may include at least one of the following: silver; carbon; and a conductive polymer. The at least one dielectric material may include at least one of the following: polydimethylsiloxane silicone; silicone rubber; and polyurethane. The at least one structured dielectric may include at least one of the following: a honeycomb structure; a hemispherical structure; nano-needle structure; and a structure including a plurality of pillars.

In another aspect, the invention is directed to a patient simulation device including: an artificial limb; a lever connected to the artificial limb; an axle connected to the lever; an adjustable friction generator disposed to the lever; a microcontroller; a friction sensor connected to at least one of the artificial limb and the lever, the friction sensor in communication with the microcontroller; and a motion sensor disposed to the axle, the motion sensor in communication with the microcontroller.

Implementations of the invention may include one or more of the following. The artificial limb may include at least one of the following: an arm; a hand; a leg; and a foot. The adjustable friction generator may include: a disc; and a disc brake. The adjustable friction generator may include: a drum; and a drum brake. The adjustable friction generator may include: a chamber including at least one granular material; and a vacuum generator configured to reduce pressure in the chamber. The adjustable friction generator may include: a chamber including at least one magnetorheological fluid; and at least one electromagnet configured to cause a change to the viscosity of at least one of the at least one magnetorheological fluid. The friction sensor may include a load cell. The friction sensor may be configured to communicate weight measurements to the microcontroller. The motion sensor may include at least one of the following: an angle sensor; a potentiometer; and an encoder. The motion sensor may be configured to communicate motion measurements to the microcontroller. The microcontroller may be configured to estimate a force applied to the artificial limb based, at least in part, on weight measurements communicated from the friction sensor. The microcontroller may be configured to estimate an angular velocity applied to the lever based, at least in part, on motion measurements communicated from the motion sensor. The microcontroller may be configured to estimate a power based, at least in part, on weight measurements communicated from the friction sensor; and motion measurements communicated from the motion sensor. The microcontroller may be configured to accept at least one data rate adjustment.

In another aspect, the invention is directed to a method of employing a patient simulation device to calibrate a hypertonicity measuring device, the hypertonicity measuring device including at least one wearable item, the method including: donning the at least one wearable item; adjusting an adjustable friction generator of the patient simulation device; employing the at least one wearable item to grasp at least a portion of an artificial limb of the patient simulation device, the artificial limb connected to a lever disposed to an axle; applying a force to the artificial limb employing the at least one wearable item; and computing a difference between the following estimated forces: a first force based, at least in part, on: weight measurements communicated from a friction sensor connected to at least one of the artificial limb and the lever; and motion measurements communicated from a motion sensor disposed to the axle; and a second force based, at least in part, on: capacitive pressure sensor data communicated from a sensor array of the hypertonicity measuring device; and motion data communicated from an inertial measurement unit of the hypertonicity measuring device.

Implementations of the invention may include one or more of the following. The method may further include applying a force great enough to overcome the static friction of the adjustable friction generator. The method may further include altering a force estimation of the second force based on the difference.

What is needed is an improved sensor for assessing hypertonicity.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

DETAILED DESCRIPTION OF EMBODIMENTS

Embodiments are employed to assess hypertonicity.

According to some of the various embodiments, a hypertonicity measuring device may comprise at least one wearable item. The at least one wearable item may comprise an article of clothing, a synthetic material, a leather material, combinations thereof, and/or the like. Examples of an article of clothing include a glove, a finger sleeve, a thumb sleeve, a wrist sleeve, a wrap, combinations thereof, and/or the like. Examples of a synthetic material include a fabric, cloth, mesh material, combinations thereof, and/or the like.

According to some of the various embodiments, a hypertonicity measuring device may comprise at least one communication pathway. The at least one communication pathway may be configured to communicate with a processing device. The at least one communication pathway may comprise at least one wireless and/or wired connection. The processing device may comprise a frequency division multiplexing circuit, a multiplexor, an analog to digital converter, an output device, a remote device, combinations thereof, and/or the like. The frequency division multiplexing circuit may employ various modulation schemes. Examples of modulation schemes include Amplitude Modulations (AM), Frequency Modulations (FM), and Phase Modulations (PM). An output device may comprise a display, a plurality of LEDs, a speaker, combinations thereof, and/or the like.

According to some of the various embodiments, a hypertonicity measuring device may comprise a sensor array. The sensor array may be disposed to at least one wearable item. The sensor array may comprise a plurality of capacitive pressure sensors. The plurality of capacitive pressure sensors may comprise at least one structured dielectric. The sensor array may be configured to communicate capacitive pressure sensor data to a processing device employing at least one communication pathway. The capacitive pressure sensor data may comprise force measurements. The force measurements may comprise constant force measurements. The force measurements may be communicated from individual capacitive pressure sensors, groups of capacitive pressure sensors, the plurality of capacitive pressure sensors, combinations thereof, and/or the like. The capacitive pressure sensor data may be time stamped. The capacitive pressure sensor data may comprise voltage measurements. A voltage may be proportional to an applied force. At least some of the plurality of capacitive pressure sensors may be configured for different dynamic range of voltages. In one embodiment, some capacitive sensors are configured to at least 48 dB of dynamic range, corresponding to at least 8 bits of resolution in the digital data. At least some of the plurality of capacitive pressure sensors may be configured for femtofarad resolution. The at least one structured dielectric may comprise a honeycomb structure, a hemispherical structure, a nano-needle structure, a structure comprising a plurality of pillars, combinations thereof, and/or the like. The hemispherical structure may be imprinted through employment of at least one nano-needle during UV curing. The nano-needle structure may comprise an upper portion of a hemispherical structure.

According to some of the various embodiments, a hypertonicity measuring device may comprise an inertial measurement unit. The inertial measurement unit may be disposed to at least one wearable item. The inertia measurement unit may comprise an accelerometer, a gyroscope, a magnetometer, combinations thereof, and/or the like. The inertial measurement unit may be configured to communicate motion data to a processing device employing at least one communication pathway. The motion data may comprise magnetic field measurements, linear acceleration measurements, angular acceleration measurements, linear velocity measurements, angular velocity measurements, combinations thereof, and/or the like. The motion data may comprise measurements of the inertial measurement unit at rest, under an acceleration, moving at a specific velocity, combinations thereof, and/or the like.

Figure 1A:
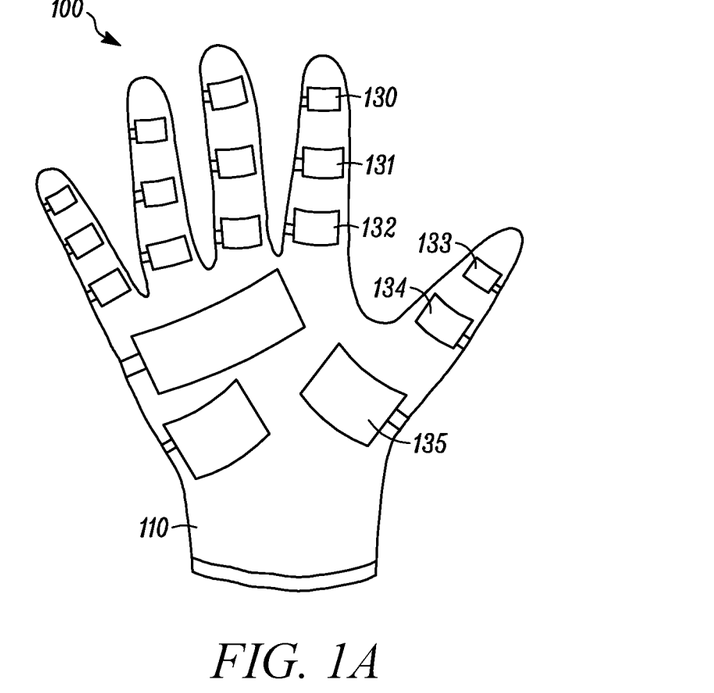
FIGS. 1A and 1B illustrate example views of a hypertonicity measuring device as per various aspects of an embodiment.
Figure 1B:
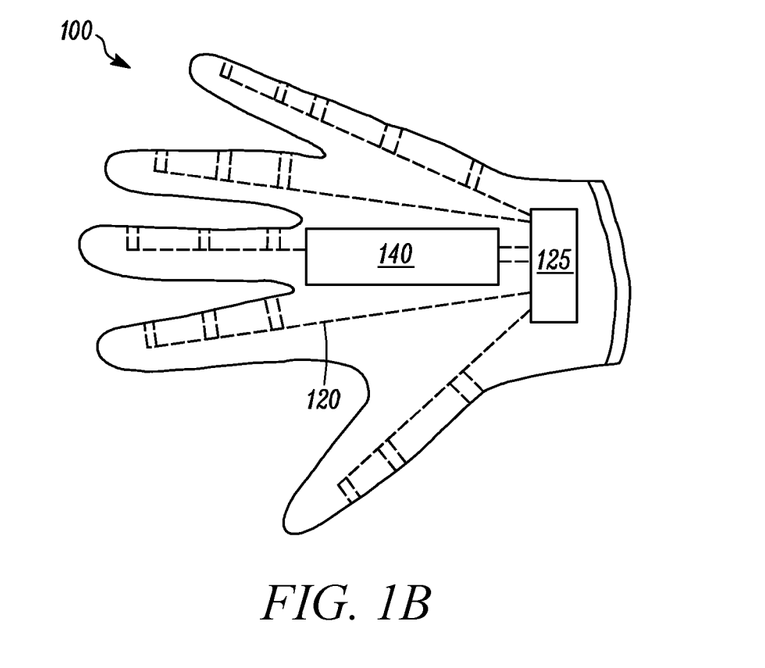

FIGS. 1A and 1B illustrate example views of a hypertonicity measuring device 100 as per various aspects of an embodiment. A bottom view (FIG. 1A) illustrates the bottom or palm side of hypertonicity measuring device 100. A top view (FIG. 1B) illustrates the back or dorsal side of hypertonicity measuring device 100. The hypertonicity measuring device 100 may comprise at least one wearable item (e.g. 110). The hypertonicity measuring device 100 may comprise at least one communication pathway 120. The at least one communication pathway 120 may comprise a connector 125. The connector may be configured for connection to a processing device. The hypertonicity measuring device 100 may comprise a sensor array. The sensor array may comprise a plurality of capacitive pressure sensors (e.g. 130, 131, 132, 133, 134, and 135). The hypertonicity measuring device 100 may comprise an inertial measurement unit 140.

Figure 2:
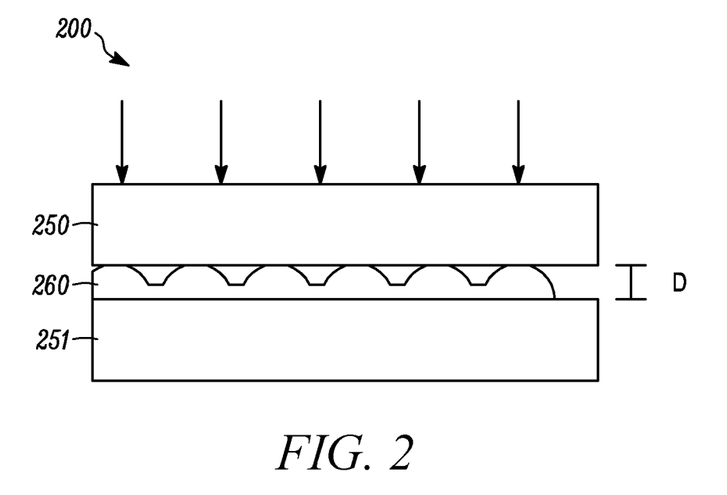
FIG. 2 illustrates an example capacitive pressure sensor as per an aspect of an embodiment.

FIG. 2 illustrates an example capacitive pressure sensor 200 as per an aspect of an embodiment. The capacitive pressure sensor 200 may comprise a first electrode 250 and a second electrode 251. The capacitive pressure sensor 200 may comprise a structured dielectric 260. The structured dielectric 260 may comprise a honeycomb structure.

Figure 3A:
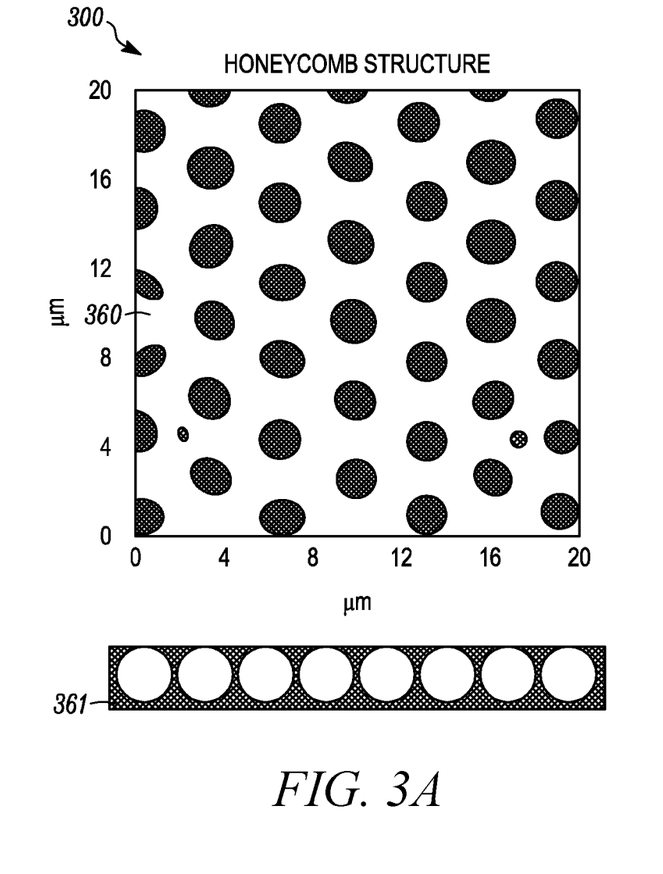
FIGS. 3A and 3B illustrate example structured dielectrics as per various aspects of an embodiment.

FIG. 3A illustrates an example structured dielectric 300 as per an aspect of an embodiment. A top down view 360 of structured dielectric 300 illustrates a honeycomb structure. A side view 361 of structured dielectric 300 illustrates the honeycomb structure.

Figure 3B:
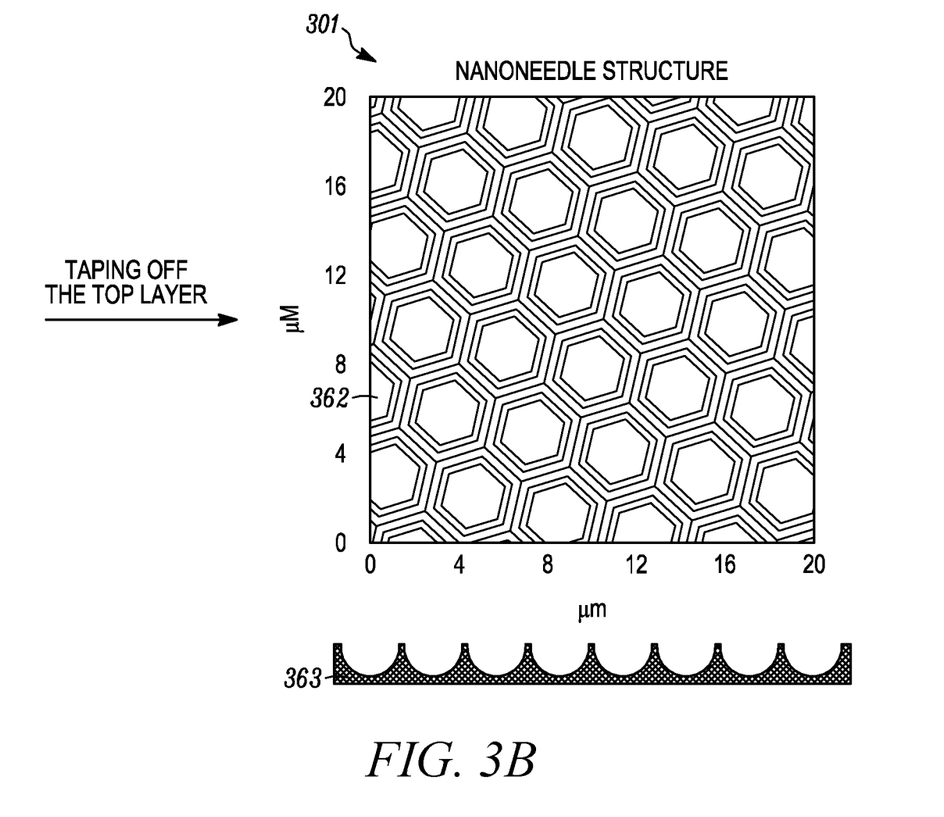

FIG. 3B illustrates an example structured dielectric 301 as per an aspect of an embodiment. A top down view 362 of structured dielectric 301 illustrates a nano-needle structure. A side view 363 of structured dielectric 301 illustrates the nano-needle structure.

According to some of the various embodiments, a processing device may be configured to estimate a result based, at least in part, on capacitive pressure sensor data and motion data. For example, for a pressure (p) and a motion (m), the processing device may be configured to compute the following function (f):

$$f(p,m).$$

The function may be related to an effort applied by a medical practitioner employing the hypertonicity measuring device to move a limb of a patient. The processing device may be configured to estimate a power based, at least in part, on the capacitive pressure sensor data and the motion data.

According to some of the various embodiments, a method of manufacturing a sensor array may comprise depositing at least one conductive material onto a wearable item. The sensor array may comprise a plurality of capacitive pressure sensors. The at least one conductive material may comprise silver, carbon, a conductive polymer, combinations thereof, and/or the like. An example of a conductive polymer is poly(3,4-ethylenedioxythiophene) polystyrene sulfonate (PEDOT:PSS). The depositing of the at least one conductive material may be configured to cause formation of a plurality of electrodes. The depositing of the at least one conductive material may be configured to cause formation of at least a portion of at least one communication pathway. The at least one communication pathway may comprise a data bus or network configured to connect at least some of the plurality of electrodes to a processing device. The at least one conductive material may be deposited through employment of a stencil patterning mask or extrusion printing. The method may comprise depositing at least one dielectric material onto the wearable item. The at least one dielectric material may comprise polydimethylsiloxane silicone, silicone rubber, polyurethane, combinations thereof, and/or the like. An example of silicone rubber is Ecoflex. The depositing of the at least one dielectric material may be configured to cause formation of at least one structured dielectric. The at least one structured dielectric may comprise a honeycomb structure, a hemispherical structure, nano-needle structure, a structure comprising a plurality of pillars, combinations thereof, and/or the like. The at least one dielectric material may be deposited through employment of a stencil patterning mask or extrusion printing. At least one of the plurality of electrodes may be laminated over or deposited over at least one of the at least one dielectric material.

Figure 4:
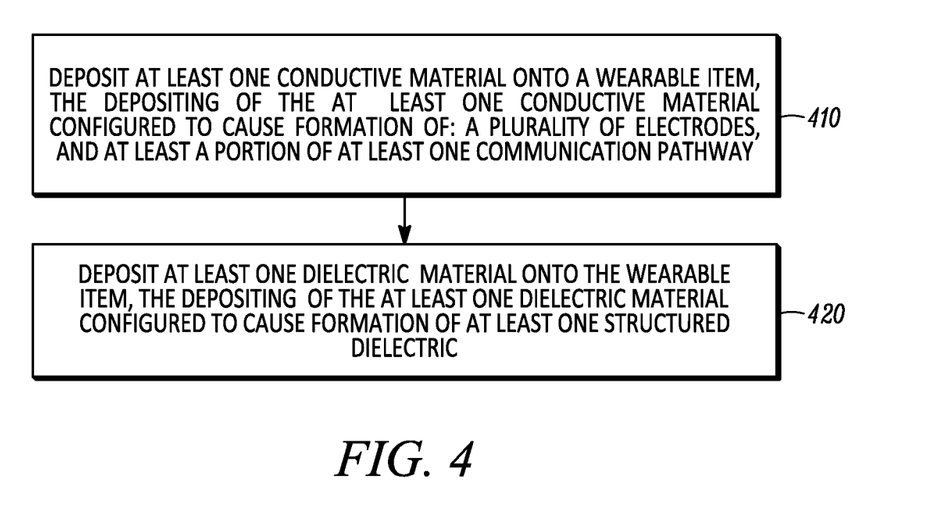
FIG. 4 is an example flow diagram of manufacturing a sensor array as per an aspect of an embodiment.

FIG. 4 is an example flow diagram of manufacturing a sensor array as per an aspect of an embodiment. At least one conductive material may be deposited on a wearable item at 410. The depositing of the at least one conductive material may be configured to cause formation of a plurality of electrodes. The depositing of the at least one conductive material may be configured to cause formation of at least a portion of at least one communication pathway. At least one dielectric material may be deposited onto the wearable item at 420. The depositing of the at least one dielectric material may be configured to cause formation of at least one structured dielectric.

Figure 5:
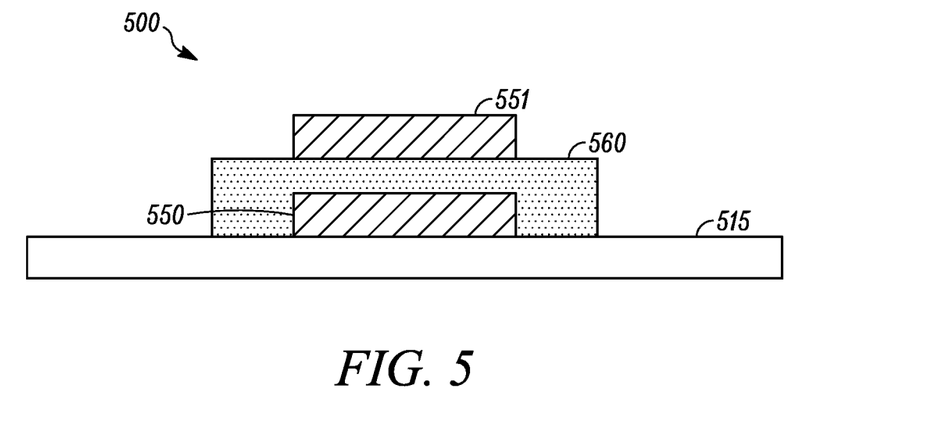
FIG. 5 is an example block diagram illustrating a manufactured capacitive pressure sensor as per an aspect of an embodiment.

FIG. 5 is an example block diagram illustrating a manufactured capacitive pressure sensor 500 as per an aspect of an embodiment. The manufactured capacitive pressure sensor 500 may be deposited on a wearable item 515. The manufactured capacitive pressure sensor 500 may comprise a first electrode 550 and a second electrode 551. The manufactured capacitive pressure sensor 500 may comprise a structured dielectric 560.

According to some of the various embodiments, a patient simulation device may comprise an artificial limb. The artificial limb may comprise an arm, a hand, a leg, a foot, combinations thereof, and/or the like. The patient simulation device may comprise a lever. The lever may be connected to the artificial limb. The patient simulation device may comprise an axle. The axle may be connected to the lever. The patient simulation device may comprise an adjustable friction generator. The adjustable friction generator may be disposed to the lever. The adjustable friction generator may be configured to apply friction to passively restrict motion. The patient simulation device may comprise a microcontroller. The patient simulation device may comprise a friction sensor. The friction sensor may be connected to the artificial limb and/or the lever. The friction sensor may comprise a load cell. The friction sensor may be in communication with the microcontroller. The patient simulation device may comprise a motion sensor. The motion sensor may comprise an angle sensor, a potentiometer, an encoder, combinations thereof, and/or the like. The motion sensor may be disposed to the axle. The motion sensor may be in communication with the microcontroller.

According to some of the various embodiments, an adjustable friction generator may comprise a disc and a disc brake. The disc may be disposed to an axle. The disc brake may comprise a caliper. The disc brake may comprise a vise or clamp. The disc brake may comprise a torque lever. The disc brake may be configured for manual, electromagnetic, pneumatic, hydraulic, combinations thereof, and/or the like adjustments. The disc brake may be adjusted through employment of a force, a voltage, pressurized air, a liquid, combinations thereof, and/or the like. The adjustable friction generator may comprise a drum and a drum brake. The drum brake may be configured for manual, electromagnetic, pneumatic, hydraulic, combinations thereof, and/or the like adjustments. The drum brake may be adjusted through employment of a force, a voltage, pressurized air, a liquid, combinations thereof, and/or the like. The adjustable friction generator may comprise a chamber. The chamber may comprise at least one granular material. The adjustable friction generator may comprise a vacuum generator configured to reduce pressure in the chamber. The chamber may be disposed to an axle. The chamber may comprise a bladder. The adjustable friction generator may be configured to regulate and/or adjust pressure. Pressure adjustment may cause friction adjustment. The chamber may comprise a magnetorheological fluid. The adjustable friction generator may comprise at least one electromagnet. The at least one electromagnet may be configured to cause a change to the viscosity of the magnetorheological fluid.

Figure 6:
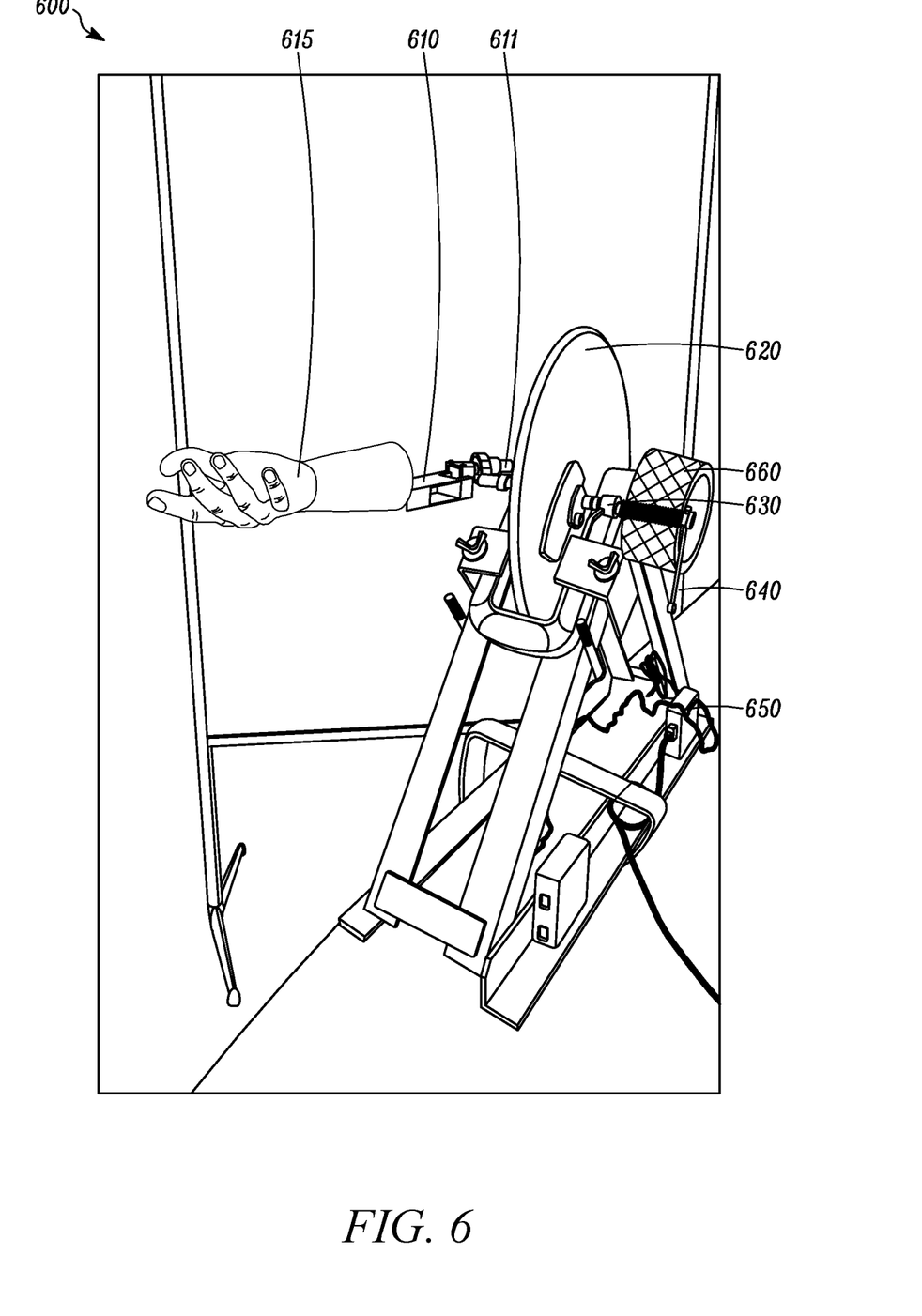
FIG. 6 illustrates an example patient simulation device as per an aspect of an embodiment.

FIG. 6 illustrates an example patient simulation device 600 as per an aspect of an embodiment. The patient simulation device 600 may comprise an artificial limb 615. The patient simulation device 600 may comprise a force sensing device 610. In one embodiment, the force sensing device 610 is a loadcell. The force sensing device 610 may be connected to the artificial limb 615. The patient simulation device 600 may comprise an axle 611. The axle 611 may be connected to the lever 610. The patient simulation device 600 may comprise an adjustable friction generator. The adjustable friction generator may be disposed to the axle 611 and/or the lever 610. The adjustable friction generator may comprise a disc 620 and a disc brake 630. The disc brake 630 may comprise a torque lever 640. The torque lever 640 may be adjusted to create different levels of friction to move the artificial limb 615. The patient simulation device 600 may comprise a microcontroller 650. The patient simulation device 600 may comprise a motion sensor 660. The motion sensor may be disposed to the axle 611.

According to some of the various embodiments, the force sensor may be configured to communicate weight measurements to a microcontroller. A motion sensor may be configured to communicate motion measurements to the microcontroller. The microcontroller may be configured to estimate a force applied to an artificial limb of a patient simulation device. The estimate may be based, at least in part, on the weight measurements communicated from the friction sensor. The microcontroller may be configured to estimate an angular velocity applied to a lever of a patient simulation device. The estimate may be based, at least in part, on motion measurements communicated from the motion sensor. The microcontroller may be configured to estimate a power. The power may be based, at least in part, on weight measurements communicated from the friction sensor. The power may be based, at least in part, on motion measurements communicated from the motion sensor. The power (P) may be represented as:

$$P = F * v$$

where $F = m*a$, and v is velocity (e.g. an angular velocity) from motion measurements, and where m is mass from weight measurements, and a is acceleration (e.g. standard of gravity).

The microcontroller may be configured to accept at least one data rate adjustment. The data rate adjustment may be employed to match a data rate of the hypertonicity measuring device. The data rate adjustment may be relative to a data rate of the hypertonicity measuring device.

According to some of the various embodiments, a method of employing a patient simulation device to calibrate a hypertonicity measuring device may comprise donning at least one wearable item. The method of employing a patient simulation device to calibrate a hypertonicity measuring device may comprise adjusting an adjustable friction generator of the patient simulation device. The method of employing a patient simulation device to calibrate a hypertonicity measuring device may comprise employing the at least one wearable item to grasp at least a portion of an artificial limb of the patient simulation device. The artificial limb may be connected to a lever of the patient simulation device. The lever may be disposed to an axle of the patient simulation device. The method of employing a patient simulation device to calibrate a hypertonicity measuring device may comprise applying a force to the artificial limb employing the at least one wearable item. The method of employing a patient simulation device to calibrate a hypertonicity measuring device may comprise computing a difference between two estimated powers: a first power and a second power. The first power may be based, at least in part, on weight measurements communicated from a force sensor connected to at least one of the artificial limb and the lever. The first power may be based, at least in part, on motion measurements communicated from a motion sensor disposed to the axle of the patient simulation device. The second power may be based, at least in part, on capacitive pressure sensor data communicated from a sensor array of the hypertonicity measuring device. The second power may be based, at least in part, on motion data communicated from an inertial measurement unit of the hypertonicity measuring device. The method of employing a patient simulation device to calibrate a hypertonicity measuring device may comprise applying a force great enough to overcome the static friction of the adjustable friction generator 640. The method of employing a patient simulation device to calibrate a hypertonicity measuring device may comprise altering a force estimation of the second force based on the difference between the two estimated forces.

Figure 7:
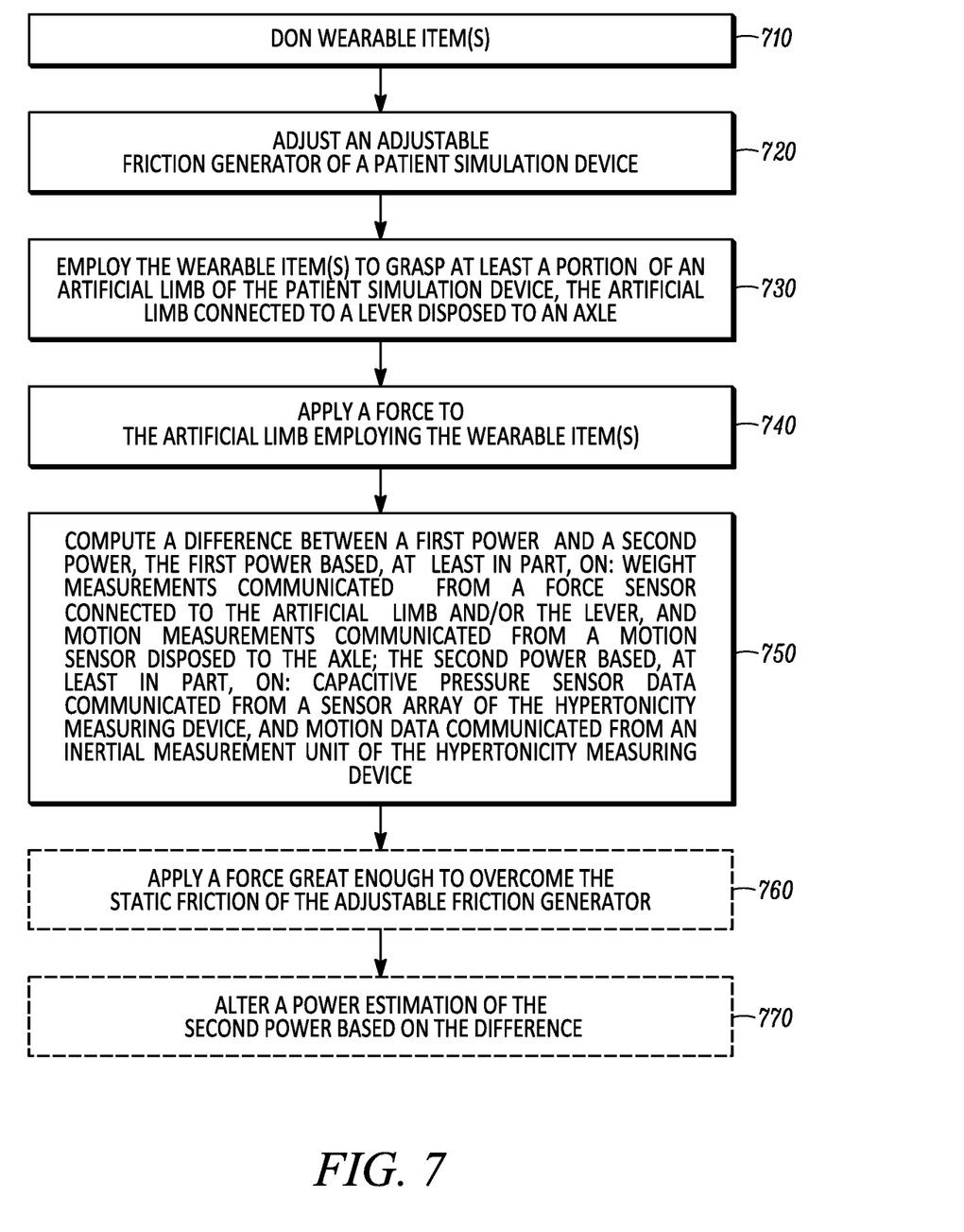
FIG. 7 is an example flow diagram of employing a patient simulation device as per various aspects of various embodiments.

FIG. 7 is an example flow diagram of employing a patient simulation device as per various aspects of various embodiments. At least one wearable item may be donned at 710. An adjustable friction generator of a patient simulation device may be adjusted at 720. The at least one wearable item may be employed to grasp at least a portion of an artificial limb of the patient simulation device at 730. The artificial limb may be connected to a lever of the patient simulation device. The lever may be disposed to an axle of the patient simulation device. A force may be applied to the artificial limb employing the at least one wearable item at 740. A difference between a first power and a second power may be computed at 750. The first power may be based, at least in part, on weight measurements communicated from a force sensor connected to the artificial limb and/or the lever. The first power may be based, at least in part, on motion measurements communicated from a motion sensor disposed to the axle. The second power may be based, at least in part, on capacitive pressure sensor data communicated from a sensor array of the hypertonicity measuring device. The second power may be based, at least in part, on motion data communicated from an inertial measurement unit of the hypertonicity measuring device. A force great enough to overcome the static friction of the adjustable friction generator may be applied at 760. A power estimation of the second power may be altered at 770. The force may be altered based on the difference.

Example

One approach to improve spasticity assessment that has been constructed is an instrumented glove in which integrated a spatially-resolved, force-dependent resistive sensor array and an inertial measurement unit (IMU) consisting of an accelerometer, gyroscope and a magnetometer [23].

The force sensor on the glove measured the contact force being applied to move a patient's limb. The level of muscular resistance to motion indicates severity of spasticity. FIGS. 1A and 1B schematically shows the force sensor integrated on to a golf glove. It has 18 sensing regions, with a total of 349 sensing elements that output a voltage proportional to the applied force. The raw output is a spatial map of 8-bit values for each sensing element. The data was collected at 20 Hz. For analysis, the sum of the output of all the sensing elements was used.

During the experiment, the glove was worn and cycles of movement with the patient were performed, such as elbow flexion and extension, and the sensor recorded the force F (Newtons) versus time.

The IMU was attached to the back of the glove as shown in FIG. 1B. It was used to characterize the hand maneuvers during clinical assessment of spasticity. In this case, only the gyroscope data was used to estimate the power needed to manipulate a limb. The IMU data was collected at 20 Hz. The angular velocity v from the gyroscope was converted to linear velocity at the location of the grip in the mock patient. The power to move the patient's limb was estimated as $F*v$.

In an initial study, five individuals with cerebral palsy volunteered to participate in this study. Participants engaged in a modified Ashworth scale assessment and then again by the same two physicians while wearing the spasticity measurement device.

In this experiment, there was substantial inter-rater variability resulting in only 27% agreement in MAS values. the data was not able to be used to validate the estimates from the glove sensors. To mitigate this, a mock patient was created that was capable of generating criterion metric (ground truth) that can be used to validate the objective numbers estimated from the glove sensors.

The mock patient had an arm structure as shown in FIG. 6. The arm has a lever connected to a disc clamped by a 5" C-clamp with stationary-bike brake pads, such that the resistance can be changed manually. The arm has an embedded load cell (model HX711) that senses the dead weight m due to the resistance set by the clamp. The force to overcome this resistance was computed as $F=m*a$, where a is standard gravity, 9.8 m/s$^2$. The term "preset resistance on the mock patient" denotes the force required to move the arm. The units are Newtons. The mock patient also has a gyroscope to sense the angular velocity v during flexion and extension, which is used to measure the power as $F*v$, in N-m/s. In experiments, the power from the mock patient sensors is measured and used to compare with the power estimated from the sensors in the glove worn by the rater.

The agreement was investigated between measured power from the mock patient and estimated power from the glove. MAS values of 1+, 2 and 3 were focused on in this study. The values of 0 and 4 are easy to assess since they correspond to normal tone and rigid limbs, respectively. Similarly, a value of 1 is also easy to assess since it is characterized by catch and release. A well-trained physician in spasticity assessment (AS) tested the mock patient and identified the range of to be 20-90 Newtons for MAS values of 1+, 2 and 3. Spasticity is a highly velocity driven response. For both glove and mock patient, the angular velocity was converted to linear velocity and the power estimated to move the patient's limb as $F*v$. The units are Newton-meters/second.

While outliers existed in both cases, the mock patient data showed better agreement with the preset resistances, compared to that of the glove. The Pearson correlation coefficient between the mock patient and the glove was 0.64. When the agreement between the mock patient and glove for flexion and extension was computed independently, the Pearson coefficients were 0.64 and 0.57 respectively. The experimenters gripped the mock patient at the wrist—flexion involved in pushing the mock patient arm, while extension involved pulling it.

Another experiment was performed with a physician (AS) performing MAS assessment for various resistance settings of the mock patient. The physician did not know the resistance setting so that he could provide an unbiased assessment.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". References to "an" embodiment in this disclosure are not necessarily to the same embodiment.

Some embodiments may employ processing hardware. Processing hardware may include one or more processors, computer equipment, embedded system, machines and/or the like. The processing hardware may be configured to execute instructions. The instructions may be stored on a machine-readable medium. According to some embodiments, a machine-readable medium (e.g. automated data medium) may be a medium configured to store data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A hypertonicity measuring device comprising:
   i. at least one wearable item;
   ii. at least one communication pathway configured to communicate with a processing device;
   iii. a sensor array, such that the sensor array is:
      1. disposed to the at least one wearable item;
      2. comprises a plurality of capacitive pressure sensors, the plurality of capacitive pressure sensors comprising at least one structured dielectric; and
      3. configured to communicate capacitive pressure sensor data to the processing device employing the at least one communication pathway; and
   iv. an inertial measurement unit:
      1. disposed to the at least one wearable item; and
      2. configured to communicate motion data to the processing device employing the at least one communication pathway; and
   wherein the processing device is configured to estimate a power based, at least in part, on:
      i. the capacitive pressure sensor data; and
      ii. the motion data.

2. The device according to claim 1, wherein the at least one wearable item comprises at least one of the following:
   i. an article of clothing;
   ii. a synthetic material; and
   iii. a leather material.

3. The device according to claim 1, wherein the processing device comprises at least one of the following:
   i. a frequency division multiplexing circuit;
   ii. a multiplexor;
   iii. an analog to digital converter;
   iv. an output device; and
   v. a remote device.

4. The device according to claim 1, wherein at least some of the plurality of capacitive pressure sensors are configured for femtofarad resolution.

5. The device according to claim 1, wherein the at least one structured dielectric comprises at least one of the following structures:
   i. a honeycomb structure;
   ii. a hemispherical structure;
   iii. nano-needle structure; and
   iv. a structure comprising a plurality of pillars.

6. The device according to claim 1, wherein the capacitive pressure sensor data comprises force measurements.

7. The device according to claim 1, wherein the inertia measurement unit comprises at least one of the following:
   i. an accelerometer;
   ii. a gyroscope; and
   iii. a magnetometer.

8. The device according to claim 1, wherein the motion data comprises measurements of at least one of the following:
   i. at least one magnetic field;
   ii. linear acceleration;
   iii. angular acceleration;
   iv. linear velocity; and
   v. angular velocity.

* * * * *